United States Patent [19]
Harbrecht et al.

[11] Patent Number: 6,019,731
[45] Date of Patent: Feb. 1, 2000

[54] INTERCONNECTION OF A SPIROMETER AND A SENSOR UNIT, WITH MACHINE READABLE INDICIUM

[75] Inventors: Brian Arthur Harbrecht, Platte City; Alvin Frederick Meyer, Kansas City, both of Mo.; Christopher Daniel Locke, Bucyrus, Kans.

[73] Assignee: Nellcor Puritan Bennett, Pleasanton, Calif.

[21] Appl. No.: 09/314,821

[22] Filed: May 19, 1999

Related U.S. Application Data

[62] Division of application No. 08/936,457, Sep. 24, 1997, Pat. No. 5,924,994.

[51] Int. Cl.[7] .................................................... A61N 5/00
[52] U.S. Cl. ...................... 600/532; 600/538; 128/205.27
[58] Field of Search ........................... 600/300, 529–540; 128/900, 205.27, 205.28, 897–899; 422/86

[56] References Cited

U.S. PATENT DOCUMENTS

| | | | |
|---|---|---|---|
| 4,991,591 | 2/1991 | Jones et al. | 600/538 |
| 5,277,196 | 1/1994 | Hankinson et al. | 600/538 |
| 5,518,002 | 5/1996 | Wolf et al. | 128/725 |
| 5,564,432 | 10/1996 | Thomson | 600/538 |
| 5,715,831 | 2/1998 | Johnson | 128/725 |
| 5,743,270 | 4/1998 | Gazzara et al. | 600/538 |

OTHER PUBLICATIONS

Nellcor Puritan Bennett brochure re Renaissance Spirometry System, 1996.

Primary Examiner—Cary O'Connor
Assistant Examiner—Michael Astorino
Attorney, Agent, or Firm—Hovey, Williams, Timmons & Collins

[57] ABSTRACT

An improved spirometry assembly (20) is provided which includes a spirometer (22) and a sensor unit (24) coupled via handle assembly (26). The spirometer (22) has a reading slot (30) as well as an optical reader (36). The sensor unit (24) includes a tab (72) having at least one characterizing indicium (76) thereon which characterizes a response parameter of the sensor unit (24) upon flow of gas therethrough. In use, the reading slot (30) receives tab (72) and the reader (36) reads the indicium (76) and generates characterizing data representative thereof which is sent to a signal processor within the spirometer (22). The assembly (20) includes a measuring device such as a pressure transducer in operative communication with the interior of the sensor unit (24) for measuring a condition therein during patient-induced gas flow and generates pressure data. The signal processor within the spirometer (22) receives both the pressure data and the sensor unit characterizing data and generates report information about a pulmonary condition of a patient.

16 Claims, 2 Drawing Sheets

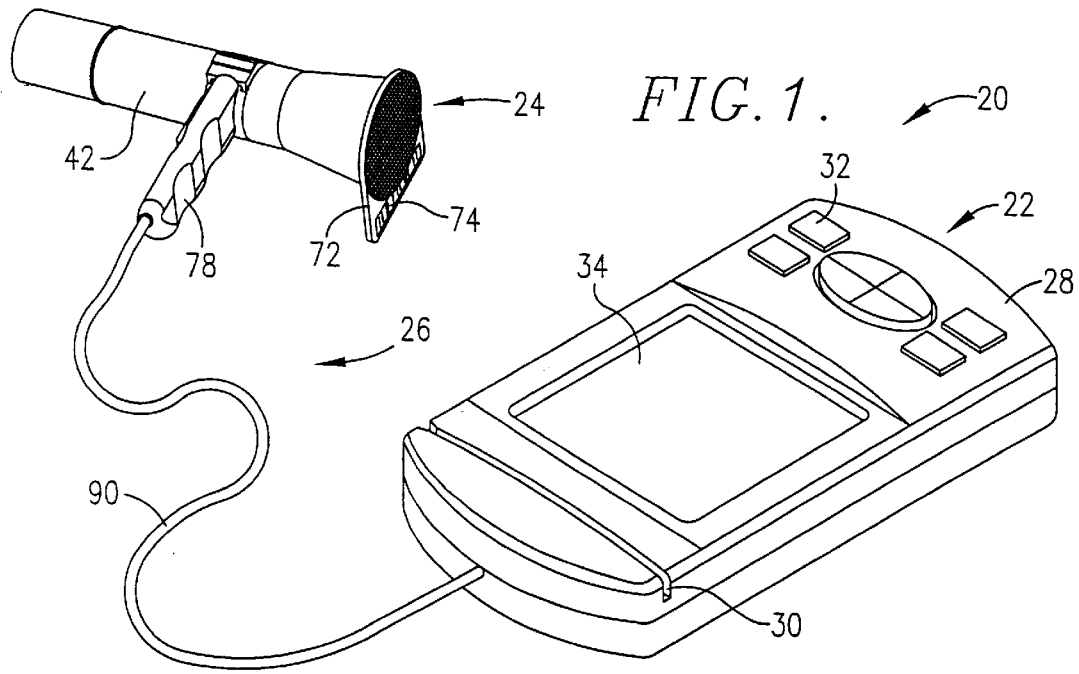
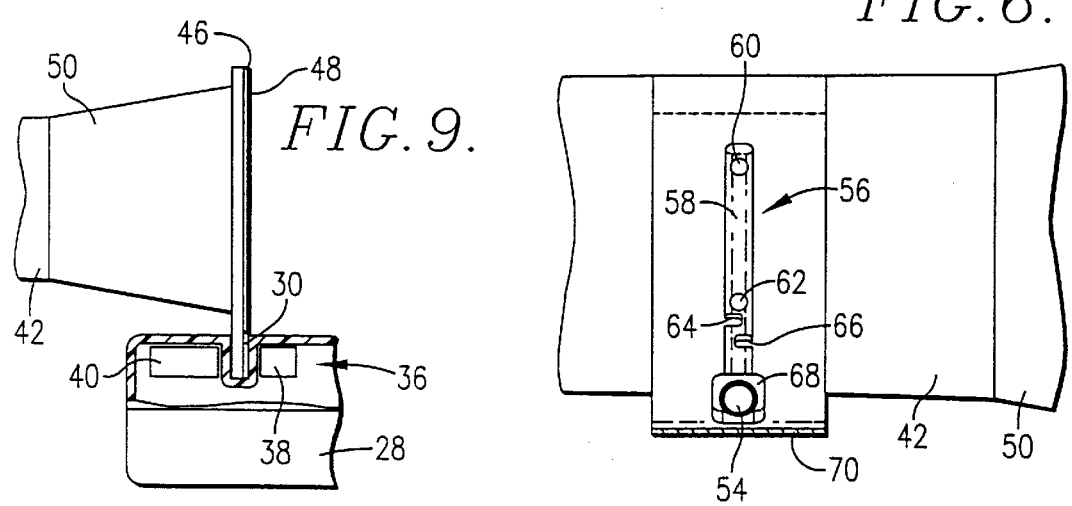
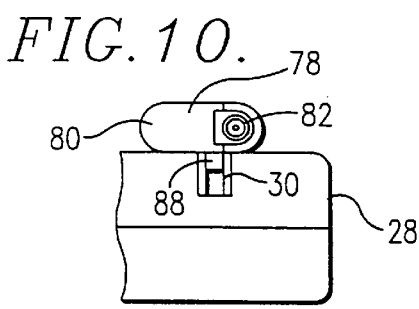
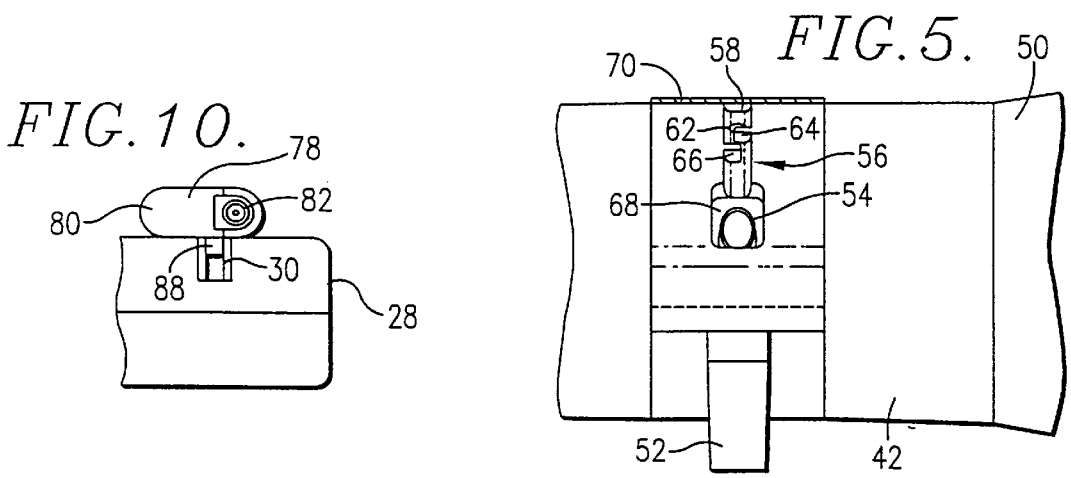

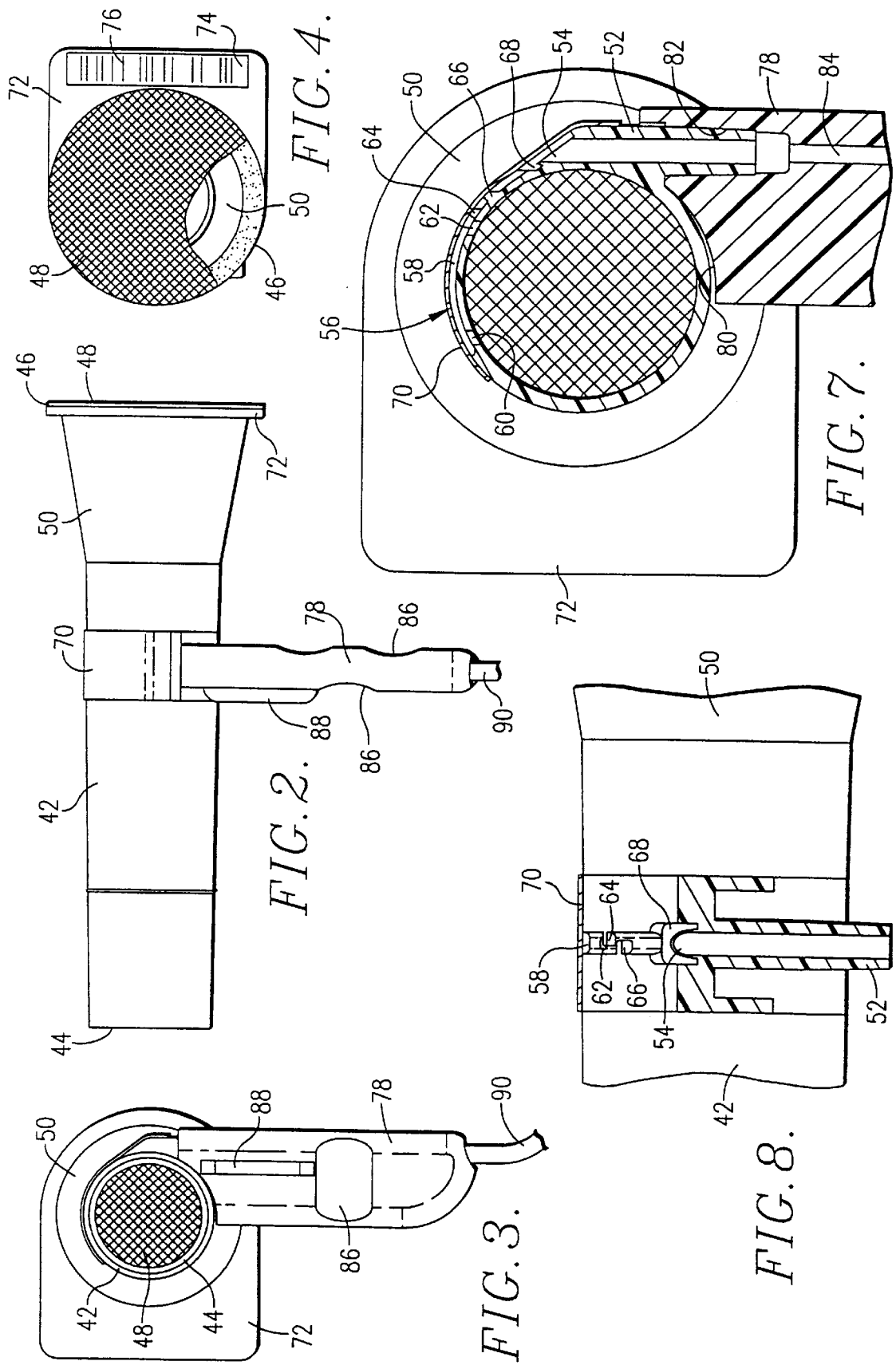

INTERCONNECTION OF A SPIROMETER AND A SENSOR UNIT, WITH MACHINE READABLE INDICIUM

RELATED APPLICATION

This is a divisional application of Ser. No. 08/936,457, now U.S. Pat. No. 5,924,994, filed Sep. 24, 1997.

BACKGROUND OF THE INVENTION

1. Field of the Invention

The present invention is broadly concerned with an improved spirometry assembly for measuring one or more patient pulmonary parameters. More particularly, the invention pertains to a spirometry assembly including a spirometer having a base equipped with a reader (e.g., an elongated reading slot with an adjacent optical reader) and a disposable tubular sensor unit having at least one characterizing indicium thereon readable by the reader. Preferably, the sensor unit has a tab including at least one characterizing indicium thereon which characterizes a response parameter of the sensor unit upon flow of gas therethrough. In use, the tab is inserted within the base slot and the characterizing indicium is read to generate characterizing data for the specific sensor unit; a measuring device (e.g., a pressure transducer) is in operative communication with the interior of the sensor unit and is used to generate condition data during patient-induced inspiratory or expiratory gas flow through the sensor. The characterizing data and condition data are sent to a signal processor which generates a report about the pulmonary condition of the patient. The preferred sensor unit is equipped with a specialized pressure chamber which minimizes the possibility of pathogen contamination during use.

2. Description of the Prior Art

Spirometry is considered to be one of the most basic and important tests that measure pulmonary function, and is used in the prevention, diagnosis, observation and therapy of many pulmonary diseases such as chronic obstructive pulmonary disease (COPD). During spirometry, a patient induces an expiratory or inspiratory gas flow through a single-use, disposable sensor tube equipped with a restrictor. The pressure conditions within the sensor tube are measured via a sensitive pressure transducer, and this data is used to calculate in a microprocessor-based signal processor various pulmonary flow conditions such as forced vital capacity (FVC), forced expiratory volume in the first second of expiration ($FEV_1$), $FEV_1$/FVC, forced expiratory volume in the third second of expiration ($FEV_3$), mean flow rate between 25% and 75% of the FVC (FEF25–75%), peak expiratory flow (PEF), forced expiratory time (FET), forced inspiratory vital capacity (FIVC), peak inspiratory flow (PIF), ratio of forced inspiratory flow at 50% of FIVC to the forced expiratory flow at 50% of FEC (FEF50%/FIF50%) and maximal voluntary ventilation (MVV).

A persistent problem with existing spirometry systems stems from the fact that the single-use spirometry sensor tubes must be individually calibrated, or characterizing data for each such sensor tube must be provided as an input to the spirometer signal processor. For example, in one widely used spirometry system sold by Nellcor Puritan Bennett Corporation under the designation "Renaissance", the individual sensor tubes having screen-type restrictors are factory-calibrated to insure that pressure conditions therein during specified gas flow rate conditions are essentially constant. Such calibration involves applying a small amount of glue to the restrictor screen, or lightly sanding the screen. As can be appreciated, such calibration operations are labor intensive and therefore relatively expensive.

It has also been known in the past to provide characterizing data with each individual sensor tube. In such systems, the user must enter the characterizing data into the spirometer so that such data can be used in the overall calculations leading to a pulmonary report. These systems suffer from the added complexity of requiring the user to enter the sensor tube characterizing data, and the possibility of data entry error which can lead to an entirely erroneous pulmonary report.

Some prior spirometry sensor tube equipment has been prone to contamination from aerosolized or other contaminants entrained within expiratory gas. This is a problem inasmuch as disease can be spread from patient-to-patient through the spirometry equipment.

SUMMARY OF THE INVENTION

The present invention overcomes the problems outlined above and provides an improved spirometry assembly for measuring a pulmonary condition of a patient. Broadly speaking, the spirometry assembly of the invention includes a base and a tubular sensor unit operatively coupled to the base. The sensor unit carries at least one characterizing indicium which characterizes a performance parameter of the sensor unit, and the spirometer has an indicium reader operatively coupled thereto for reading the sensor unit indicium and providing such information to the signal processor of the spirometer. Preferably, the base presents an elongated reading slot and is equipped with a reader adjacent the reading slot. The sensor unit comprises an elongated tubular element having a reading tab, the latter having at least one characterizing indicium which characterizes a response parameter of the tubular element upon measured flow of gas therethrough. In use, the reading slot receives the tab and the reader reads the indicium information and generates characterizing data which is sent to a microprocessor-based signal processor housed within the base. Next, the patient induces a gas flow (either inspiratory or expiratory) through the tubular element, and a measuring device in operative communication with the interior of the element measures a condition therein and generates representative condition data which is also sent to the signal processor. In the signal processor, the characterizing data and condition data is used to generate report information about the pulmonary condition of the patient.

In preferred forms, the measuring device is in the form of the pressure transducer and AC/DC converter which is housed within the base along with the signal processor. Thus, during the patient-induced pulmonary gas flow, the pressure conditions over time within the tubular element are measured. Pressure condition data is then mathematically converted, using the specific characterizing data for the sensor unit used, to give a pulmonary report about the patient, generally in terms of pulmonary flow information.

The preferred reader within the spirometer base comprises a light emitting diode (LED) and a photo detector respectively positioned on opposite sides of the reading slot. With this type of reader, the sensor unit tab must be at least translucent (and may of course be transparent) to permit passage of light therethrough. It has been found that characterizing data in the form of a series of spaced apart bar-like elements can be very accurately read by the reader of this preferred type. Accordingly, in preferred practice, a transparent polyester strip with such bar element characterizing information is applied to one face of each sensor unit tab using an acrylic adhesive applied to the underside of the strip during manufacture of the sensor unit.

The preferred sensor unit is also equipped with a specialized pressure chamber which has been designed to minimize the possibility of pathogen contamination. In particular, the tubular element includes a pressure chamber in operative communication with the interior thereof. The pressure chamber is in the form of an elongated, concave channel formed in the outer wall of the tubular element, with at least one aperture communicating the channel with the interior of the tubular element; a web of flexible synthetic resin tape is applied over the channel to complete the pressure chamber. In order to impede the passage of contaminants along the length of the pressure chamber, one or more upstanding, inwardly extending obstructions or diverters are located within the channel, thus causing any such contaminants to traverse a tortuous or serpentine path.

The sensor unit also has an elongated, tubular connection nipple or stem having an inlet opening in communication with the channel. A recessed region or trap surrounds the inlet opening of the stem for collection of contaminants therein to prevent such contaminants from passing into the stem, thus providing a further degree of contamination prevention.

BRIEF DESCRIPTION OF THE DRAWINGS

FIG. 1 is a perspective view of a spirometry assembly in accordance with the invention, made up of a spirometer and a sensor unit operatively coupled thereto;

FIG. 2 is a side elevational view of the preferred sensor unit of the invention;

FIG. 3 is an end view of the sensor unit illustrated in FIG. 2, viewing the inlet end thereof;

FIG. 4 is an end view of the sensor unit of FIG. 2, viewing the tab end thereof and with the restrictor screen partially broken away to illustrate the internal design of the sensor unit;

FIG. 5 is a fragmentary side view of the sensor unit, shown with a portion of the web normally covering the pressure chamber broken away to reveal details of construction of the pressure chamber;

FIG. 6 is a fragmentary top view of the sensor unit, with a portion of the web normally covering the pressure chamber removed;

FIG. 7 is an enlarged, fragmentary vertical sectional view of the sensor unit illustrating in detail the pressure chamber and outlet stem;

FIG. 8 is an enlarged, fragmentary vertical sectional view taken through the outlet stem as depicted in FIG. 7;

FIG. 9 is a fragmentary view illustrating the sensor unit tab inserted within the spirometer reading slot; and FIG. 10 is a fragmentary side view illustrating the sensor unit handle flange inserted within the reading slot during storage and transportation of the spirometry assembly.

DETAILED DESCRIPTION OF THE PREFERRED EMBODIMENT

Turning now to the drawings, and particularly FIG. 1, a spirometry assembly 20 is illustrated which broadly includes a spirometer 22 as well as a sensor unit 24 operatively coupled thereto via a handle assembly 26.

The spirometer 20 is in the form of a hand-held, portable base 28 equipped with an elongated reading slot 30, control and input buttons 32 and output screen 34. The base 28 has a reader 36 (see FIG. 9) preferably in the form of a light emitting diode 38 and photodetector 40 respectively disposed on opposite sides of reading slot 30. In addition, a pressure transducer and AC/DC converter are housed within base 28, along with a microprocessor-type signal processor and associated circuitry, all of such hardware being of conventional design.

The sensor unit 24 includes a single-use, disposable tubular element 42 having an input end 44 and an opposed output end 46 covered with a screen-type restrictor 48 attached by sonic welding. As shown, the body 42 is of slightly tapered design along the majority of its length, but has a frustoconical endmost section 50 leading to output end 46.

As best seen in FIGS. 5–8, an elongated, tubular, approximately tangentially oriented integral outlet stem 52 is provided on element 42 and presents an uppermost, obliquely oriented circular inlet opening 54. The inlet opening 42 communicates with a pressure chamber 56 in the form of an elongated, cross-sectionally concave channel 58 which is integrally formed in the wall of element 42. A pair of spaced apertures 60, 62 serve to communicate chamber 56 with the interior of element 42. As seen in FIGS. 6 and 7, the channel 58 has a pair of axially spaced apart, upstanding flow diverters 64, 66 therein between aperture 62 and inlet opening 54. It will be noted that the diverters 64, 66 cooperatively present a tortuous path for any contaminants which may pass through the apertures 60, 62 during use of sensor unit 24. In addition, the element 42 is configured to present a trap or recessed area 68 around stem inlet opening 54. This provides a still further protection against contaminants entering stem 52, i.e., such contaminants are contained and trapped within the recessed area 68 beneath the inlet opening 54. In order to complete the pressure chamber 56, a web of flexible adhesive synthetic resin material 70 is applied over channel 58 and inlet opening 54.

An integral, laterally projecting tab 72 extends from the output end 46 of tubular element 42. The tab 72 is dimensioned to fit within reading slot 30, and supports thereon a mylar strip 74 having a series of elongated bar-like markings 76. At least the portion of tab 72 supporting strip 74, and strip 74 itself, are translucent to allow passage of light therethrough. The strip 74 having the markings 76 is applied to each individual element 42 during manufacture as characterizing indicia for the respective element. Specifically, during manufacture, each individual element 42 is tested by passing a precisely monitored flows of gas therethrough. The pressure conditions generated within the respective element 42 under such test conditions are measured and characterizing indicia, in the form of the strip 74 with markings 76 thereon, is printed. This printed strip is then applied to the tab 72.

The preferred tubular element 42 is fabricated as an integral unit and is formed of an appropriate styrene-butadiene copolymer material such as K-Resin KR01, KR03 or BK10 sold by the Phillips Chemical Company. The restrictor 48 is formed of commercially available wire cloth having from 200×200 to 400×400 mesh count per inch with a percent open area ranging from about 29–46%.

The handle assembly 26 includes an elongated synthetic resin handle body 78 which is adapted to detachably support individual sensor units 24. To this end, the handle body 78 includes an upper arcuate surface 80 which generally conforms with the curvature of tubular element 42, as well as a stem-receiving bore 82 sized to frictionally receive stem 52 (see FIG. 7). The handle body also has an elongated passageway 84 extending from bore 82 to the bottom thereof. As best seen in FIGS. 2 and 3, the handle body 78 has appropriately sized and located grips 86 as well as an outwardly projecting, flange 88.

The handle assembly 26 also includes an elongated, flexible conduit or tube 90. One end of the tube 90 is secured to handle body 78 by means of a barb connector (not shown) so that the tube is in communication with passageway 84. The other end of tube 90 is connected to the underside of base 28 through a port leading to the pressure transducer within the base.

In the use of assembly 20, the operator first obtains a sensor unit 24 and the latter is attached to handle body 78 by insertion of stem 52 into bore 82. The base 28 is then activated by pressing the appropriate control button, and the tab 72 is inserted within reading slot 30. The tab is passed along the length of the slot past reader 36 so that the reader can identify the location of the markings 76 on the strip 74. This characterizing indicia for the respective sensor unit 24 is then sent to the memory associated with the base signal processor.

In the next step, a patient induces gas flow through the tubular element 42 by either blowing into or sucking air through the inlet end 44. The patient is normally asked to exhale into or inhale through the end 44 for a specified period of time, such as three seconds. This in turn generates positive or negative pressure conditions within the interior of tube 42 and chamber 56. The pressure conditions within the chamber 56 are measured multiple times over the exhale/inhale period by the base-mounted transducer, owing to the communication established between the transducer and chamber 56 through tube 90, passageway 84, bore 82 and stem 52. The transducer thus generates pressure condition data and this is also sent to the signal processor.

The signal processor receives the characterizing data and the pressure condition data and calculates report information about the pulmonary condition of the patient. The mathematical algorithms used to generate the report information are known and a number of different algorithms can be employed. For example, the characterizing and pressure condition data can be used in the following general equation to derive desired pulmonary flow information by solving for F:

$$K_1(F)+K_1(F^2)+K_3(F^3)=P_T$$

where $P_T$ is representative of the measured pressure conditions within the tube 42, F is the pulmonary flow and $K_1$, $K_2$ and $K_3$ are characterizing indicia encoded by the markings 76 during manufacture of the particular sensing unit 24. The output from the signal processor is displayed on output screen 34 of base 28 and can also be transferred via a conventional cable to an output printer.

After a spirometry test is completed, the unit 24 used for that test is detached from handle 78 and discarded. If a new test session is to be commenced for a different patient, a fresh sensor unit 24 is then attached to the handle 78 and the above process is repeated. However, if the operator needs to move to a different location for the next session, the handle unit 78 is grasped and flange 88 thereof is pressed into slot 30 as shown in FIG. 10. The flange 88 is configured so that the handle unit 78 is frictionally held against the body 28. As such, the entire assembly can be conveniently stored and handled until it is next to be used.

The assembly 20 can be used to develop any or all of the conventionally used pulmonary function test data, e.g., FVC $FEV_1$, $FEV_1/FVC$, $FEV_3$, FEF25–75%, PEF, FET, FIVC, PIF, FEF50%/FIF50% and MVV. In addition, while in the embodiment illustrated the pressure transducer is housed within the base 28, it would be feasible to alternately mount the transducer within the handle unit 78. In such a case, an electrical connection would be established between the transducer and the microprocessor within the base 28.

We claim:

1. A spirometry sensor unit comprising an elongated, tubular element presenting a pair of ends, one of said ends permitting a patient to induce a pulmonary air flow through the element, an elongated tab projecting from a surface of said tubular element and presenting a width greater than the thickness thereof and an outer margin spaced from said element, said tab carrying at least one machine readable indicium which provides characterizing information about the spirometry performance of the sensor unit, and an elongated, tubular connection stem separate and axially spaced from said projecting tab for permitting interconnection of said sensor unit with a handle, said tubular connector in communication with the interior of said tubular element.

2. The sensor unit of claim 1, said tab formed of a light-transmitting material, said indicium readable by locating the tab between a reader comprising a light-emitting diode and an opposed photo detector.

3. The sensor unit of claim 2, said tab being transparent.

4. The sensor unit of claim 1, said indicium comprising a series of spaced apart, machine readable bars.

5. The sensor unit of claim 1, including a pressure chamber on said sensor unit and in operative communication with the interior of the tubular element.

6. The sensor unit of claim 5, said pressure chamber including an elongated, concave channel formed in the outer wall of said tubular element with at least one aperture communicating said channel with the interior of the tubular element, there being at least one upstanding diverter within said channel for causing any contaminants therein to traverse a tortuous path along the length of the channel.

7. The sensor unit of claim 6, said connection stem extending from said tubular element and in communication with said channel, said connection stem presenting an inlet opening adjacent said channel, there being a recessed region surrounding said inlet opening for collection of contaminants and preventing such contaminants from passing into said stem.

8. The sensor unit of claim 6, including a web of adhesively secured material disposed over said channel.

9. The sensor unit of claim 1, said stem presenting a longitudinal axis, said tab projecting from said tubular element in a direction transverse relative to said stem longitudinal axis.

10. In combination:

a spirometry sensor unit comprising an elongated, tubular element presenting a pair of ends, one of said ends permitting a patient to induce a pulmonary air flow through the element, an elongated tab projecting from a surface of said tubular element and presenting a width greater than the thickness thereof and an outer margin spaced from said element, said tab carrying at least one machine readable indicium which provides characterizing information about the spirometry performance of the sensor unit, and a connector separate and axially spaced from said projecting tab; and a handle including structure configured to mate with said sensor unit connector in order to interconnect the handle and sensor unit and support the sensor unit during use thereof, said handle being axially spaced from said tab along the length of said sensor unit.

11. The sensor unit of claim 10, said tab formed of a light-transmitting material, said indicium readable by locating the tab between a reader comprising a light-emitting diode and an opposed photo detector.

12. The sensor unit of claim 11, said tab being transparent.

13. The sensor unit of claim 10, said indicium comprising a series of spaced apart, machine readable bars.

14. The sensor unit of claim 10, including a pressure chamber on said sensor unit and in operative communication with the interior of the tubular element.

15. The sensor unit of claim 14, said pressure chamber including an elongated, concave channel formed in the outer wall of said tubular element with at least one aperture communicating said channel with the interior of the tubular element, there being at least one upstanding diverter within said channel for causing any contaminants therein to traverse a tortuous path along the length of the channel.

16. The sensor unit of claim 10, said connector comprising an elongated, tubular connection stem extending from said tubular element and in communication with said channel, said connection stem presenting an inlet opening adjacent said channel, there being a recessed region surrounding said inlet opening for collection of contaminants and preventing such contaminants from passing into said stem.

* * * * *